US007875310B2

(12) United States Patent
Rickey et al.

(10) Patent No.: US 7,875,310 B2
(45) Date of Patent: *Jan. 25, 2011

(54) RESIDUAL SOLVENT EXTRACTION METHOD AND MICROPARTICLES PRODUCED THEREBY

(75) Inventors: Michael E. Rickey, Loveland, OH (US); J. Michael Ramstack, Lunenburg, MA (US); Rajesh Kumar, Marlborough, MA (US)

(73) Assignee: Alkermes, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/382,637

(22) Filed: Mar. 20, 2009

(65) Prior Publication Data

US 2009/0194894 A1 Aug. 6, 2009

Related U.S. Application Data

(63) Continuation of application No. 11/785,638, filed on Apr. 19, 2007, now Pat. No. 7,524,530, which is a continuation of application No. 11/312,371, filed on Dec. 21, 2005, now Pat. No. 7,223,440, which is a continuation of application No. 10/956,092, filed on Oct. 4, 2004, now abandoned, which is a continuation of application No. 09/942,631, filed on Aug. 31, 2001, now Pat. No. 6,824,822.

(51) Int. Cl.
*B01J 13/12* (2006.01)
*A61K 38/00* (2006.01)

(52) U.S. Cl. .................. 427/213.32; 264/4.33; 530/350; 514/12

(58) Field of Classification Search .................. None
See application file for complete search history.

(56) References Cited

U.S. PATENT DOCUMENTS

| | | | |
|---|---|---|---|
| 3,523,906 A | 8/1970 | Vrancken et al. |
| 3,691,090 A | 9/1972 | Kitajima et al. |
| 3,737,337 A | 6/1973 | Schnoring et al. |
| 3,773,919 A | 11/1973 | Boswell et al. |
| 3,891,570 A | 6/1975 | Fukushima et al. |
| 3,960,757 A | 6/1976 | Morishita et al. |
| 4,221,862 A | 9/1980 | Naito et al. |
| 4,384,975 A | 5/1983 | Fong |
| 4,389,330 A | 6/1983 | Tice et al. |
| 4,530,840 A | 7/1985 | Tice et al. |
| 4,737,437 A | 4/1988 | Gutsell et al. |
| 4,818,517 A | 4/1989 | Kwee et al. |
| 4,840,896 A | 6/1989 | Reddy et al. |
| 4,923,805 A | 5/1990 | Reddy et al. |
| 4,940,588 A | 7/1990 | Sparks et al. |
| 5,019,400 A | 5/1991 | Gombotz et al. |
| 5,066,436 A | 11/1991 | Komen et al. |
| 5,126,147 A | 6/1992 | Silvestri et al. |
| 5,204,108 A | 4/1993 | Illum |
| 5,225,205 A | 7/1993 | Orsolini |
| 5,271,945 A | 12/1993 | Yoshioka et al. |
| 5,312,335 A | 5/1994 | McKinnon et al. |
| 5,336,505 A | 8/1994 | Ng et al. |
| 5,385,738 A | 1/1995 | Yamahira et al. |
| 5,407,609 A | 4/1995 | Tice et al. |
| 5,424,286 A | 6/1995 | Eng |
| 5,428,024 A | 6/1995 | Chu et al. |
| 5,478,564 A | 12/1995 | Wantier et al. |
| 5,541,172 A | 7/1996 | Labric et al. |
| 5,589,167 A | 12/1996 | Cleland et al. |
| 5,630,796 A | 5/1997 | Bellhouse et al. |
| 5,639,640 A | 6/1997 | Reddy et al. |
| 5,650,173 A | 7/1997 | Ramstack et al. |
| 5,654,008 A | 8/1997 | Herbert et al. |
| 5,654,010 A | 8/1997 | Johnson et al. |
| 5,656,297 A | 8/1997 | Bernstein et al. |
| 5,656,299 A | 8/1997 | Kino et al. |
| 5,658,593 A | 8/1997 | Orly et al. |
| 5,667,808 A | 9/1997 | Johnson et al. |
| 5,688,801 A | 11/1997 | Mesens et al. |
| 5,707,644 A | 1/1998 | Illum |
| 5,747,058 A | 5/1998 | Tipton et al. |
| 5,767,251 A | 6/1998 | Reddy et al. |
| 5,770,231 A | 6/1998 | Mesens et al. |
| 5,792,477 A | 8/1998 | Rickey et al. |
| 5,871,778 A | 2/1999 | Kino et al. |
| 5,916,598 A | 6/1999 | Rickey et al. |
| 5,942,253 A | 8/1999 | Gombotz et al. |
| 5,945,126 A | 8/1999 | Thanoo et al. |
| 5,965,168 A | 10/1999 | Mesens et al. |
| 5,981,719 A | 11/1999 | Woiszwillo et al. |
| 5,989,463 A | 11/1999 | Tracy et al. |

(Continued)

FOREIGN PATENT DOCUMENTS

EP      0 052 510      5/1982

(Continued)

OTHER PUBLICATIONS

Akers, et al., "Formulation Design and Development of Parenteral Suspensions," Journal of Parenteral Science & Technology, 41(3): 88-96 (1987).

Alonso, et al., "Determinants of Release Rate of Tetanus Vaccine from Polyester Microspheres," Pharmaceutical Research, 10(7): 945-953 (1993).

Beck, et al., "Poly(DL-Lactide-co-glycolide)/Northisterone Microcapsules: An Injectable Biodegradable Contraceptive," Biology of Reproduction, 28(1): 186-195 (1983).

(Continued)

*Primary Examiner*—Anand U Desai
(74) *Attorney, Agent, or Firm*—Covington & Burling LLP; Andrea G. Reister, Esq.; Melody Wu, Esq.

(57) ABSTRACT

Methods for preparing microparticles having reduced residual solvent levels. Microparticles are contacted with a non-aqueous washing system to reduce the level of residual solvent in the microparticles. Preferred non-aqueous washing systems include 100% ethanol and a blend of ethanol and heptane. A solvent blend of a hardening solvent and a washing solvent can be used to harden and wash microparticles in a single step, thereby eliminating the need for a post-hardening wash step.

12 Claims, 3 Drawing Sheets

U.S. PATENT DOCUMENTS

| | | | |
|---|---|---|---|
| 6,110,503 | A | 8/2000 | Rickey et al. |
| 6,113,947 | A | 9/2000 | Cleland et al. |
| 6,120,787 | A | 9/2000 | Gustafsson et al. |
| 6,190,702 | B1 | 2/2001 | Takada et al. |
| 6,194,006 | B1 | 2/2001 | Lyons et al. |
| 6,217,893 | B1 | 4/2001 | Pellet et al. |
| 6,284,283 | B1 | 9/2001 | Costantino et al. |
| 6,291,013 | B1 | 9/2001 | Gibson et al. |
| 6,368,630 | B1 | 4/2002 | Bernstein et al. |
| 6,369,116 | B1 | 4/2002 | Wong et al. |
| 6,465,425 | B1 | 10/2002 | Tracy et al. |
| 6,495,164 | B1 | 12/2002 | Ramstack et al. |
| 6,548,302 | B1 | 4/2003 | Mao et al. |
| 6,558,702 | B2 | 5/2003 | Dasch et al. |
| 6,749,866 | B2 | 6/2004 | Bernstein et al. |
| 6,824,822 | B2 | 11/2004 | Rickey et al. |
| 7,223,440 | B2 | 5/2007 | Rickey et al. |
| 2003/0003074 | A1 | 1/2003 | Zentner et al. |
| 2003/0004100 | A1 | 1/2003 | Dasch et al. |
| 2003/0087820 | A1 | 5/2003 | Young et al. |
| 2003/0118660 | A1 | 6/2003 | Rickey et al. |
| 2003/0133979 | A1 | 7/2003 | Burke et al. |
| 2004/0121009 | A1 | 6/2004 | Dasch et al. |
| 2004/0208929 | A1 | 10/2004 | Costantino et al. |
| 2004/0208989 | A1 | 10/2004 | Lee et al. |
| 2004/0228833 | A1 | 11/2004 | Costantino et al. |
| 2005/0079224 | A1 | 4/2005 | Rickey et al. |
| 2006/0011657 | A1 | 1/2006 | Wright et al. |
| 2006/0099271 | A1 | 5/2006 | Rickey et al. |
| 2007/0196499 | A1 | 8/2007 | Rickey et al. |
| 2008/0050447 | A1 | 2/2008 | Rickey et al. |

FOREIGN PATENT DOCUMENTS

| | | |
|---|---|---|
| EP | 0 302 582 | 2/1989 |
| EP | 0 486 959 | 5/1992 |
| EP | 0 521 586 | 1/1993 |
| EP | 0 831 773 | 12/1999 |
| WO | WO-89/03678 | 5/1989 |
| WO | WO-90/13285 | 11/1990 |
| WO | WO-90/13361 | 11/1990 |
| WO | WO-90/13780 | 11/1990 |
| WO | WO-92/19241 | 11/1992 |
| WO | WO-94/10982 A1 | 5/1994 |
| WO | WO-95/13799 | 5/1995 |
| WO | WO-96/36317 | 11/1996 |
| WO | WO-96/40049 | 12/1996 |
| WO | WO-97/41837 A1 | 11/1997 |
| WO | WO-99/12549 | 3/1999 |
| WO | WO-00/59476 | 10/2000 |
| WO | WO-00/66087 | 11/2000 |
| WO | WO-01/19345 A1 | 3/2001 |
| WO | WO-01/28525 A1 | 4/2001 |
| WO | WO-02/083096 A | 10/2002 |
| WO | WO-03/020245 | 3/2003 |
| WO | WO-03/066585 | 8/2003 |
| WO | WO-2004/034975 A2 | 4/2004 |
| WO | WO-2004/035754 A2 | 4/2004 |
| WO | WO-2004/035762 | 4/2004 |
| WO | WO-2004/036186 | 4/2004 |
| WO | WO-2004/103342 B2 | 12/2004 |

OTHER PUBLICATIONS

Bodmeier, et al., "Solvent selection in the preparation of poly(DL-lactide) microspheres prepared by the solvent evaporation method," International Journal of Pharmaceutics, 43:179-186 (1988).

Carrasquillo, Karen G. et al., "Non-aqueous encapsulation of excipient-stabilized spray-freezed dried BSA into poly (lactide-co glycolide) microspheres results in release of native protein," Journal of Controlled Release (2001) 76:199-208.

Castellanos, Ingrid J. et al., Prevention of structural perturbations and aggregation upon encapsulatin of bovine serum albumin into poly (lactide-co glycolide) microspheres using the solid-in-oil-water technique, Journal of Pharmacy and Pharmacology (2001) 53:1099-1107.

Cha, et al., "A One-Week Subdermal Delivery System for L-Methadone Based on Biodegradable Microcapsules," Journal of Controlled Release, 7: 69-78 (1988).

Cha, et al., "The Acceleration of Degradation-Controlled Drug Delivery from Polyester Microspheres," Journal of Controlled Release, 8: 259-265 (1989).

Cohen, et al., Controlled Delivery Systems for Proteins Based on Poly(Lactic/Glycolic Acid) Microspheres, Pharmaceutical Research, 8(6):713-720, 1991.

Conti, et al., "Use of polylactic acid for the preparation of microparticulate drug delivery systems," Journal of Microencapsulation, 9(2): 153-166 (1992).

Costantino, Henry R. et al., Protein Spray Freeze Drying. 2. Effect of formulation variables on particle size and stability, J. Pharm. Sci. (2002) 91:388-395.

Costantino, Henry R. et al., Relationship between encapsulated drug particle size and initial release of recombinant human growth hormone from biodegradable microspheres, J. Pharm. Sci (2004) 93(10):2624-2634.

Creighton, Thomas E., "In Proteins: Structures and Molecular Principles," published by W.H. Freeman & Company, NY, pp. 149-150, 1984.

Elvassore, Nicola et al., "Production of Insulin-Loaded Poly(Ethylene Glycol)/Poly(I-Lactide) (PEG/PLA) Nanoparticles by Gas Antisolvent Techniques," J. of Pharmaceutical Sci., 90(10):1628 (Oct. 2001).

Evert J.P., van Santbrink and Bart C.J.M. Fauser, "Urinary Follicle-Stimulating Hormone for Normogonadotropic Colomiphene-Resistant Anovulatory Infertility: Prospective, Randomized Comparison between Low Dose Step-Up and Step-Down Dose Regimens," J. Clin. Endocrinology Metab., 82(11):3597-3602 (1997).

Hodgman, et al., Eds., Handbook of Chemistry and Physics, 35th Edition, 1024-1025 (1953).

Jalil, et al., "Biodegradable poly(lactic acid) and poly(lactide-co-glycolide) microcapsules: problems associated with preparative techniques and release properties," Journal of Microencapsulation, 7(3):297-319 (1990).

Lee et al., "The Stabilization of Proteins by Sucrose," J. Biological Chem, 256(14):7193-7201 (1981).

Li, et al., "Prediction of solvent removal profile and effect on properties for peptide-loaded PLGA microspheres prepared by solvent extraction/evaporation method," Journal of Controlled Release, 37(3):199-214 (1995).

Lucke et al., Peptide Acylation by Poly(beta-Hydroxy Esters), Pharmaceutical Research, 19(2):175-181 (2002).

Maa, et al., "Liquid-Liquid emulsification by static mixers for use in microencapsulation," Journal of Microencapsulation, 13(4)419-433 (1996).

Maulding, et al., "Biodegradable microcapsules: Acceleration of Polymeric Excipient Hydrolytic Rate by Incorporation of a Basic Medicament," Journal of Controlled Release, 3:103-117 (1986).

Mehta, Rahul C. et al., Peptide containing microspheres from low molecular weight and hydrophilic poly (d,l—lactide-coglycolide), Journal of Controlled Release, 41:249-257 (1996).

Perez, Carolina et al., Recent trends in stabilizing protein structure upon encapsulation and release from bioerodible polymers, Journal of Pharmacy and Pharmacology (2002) 54:301-313.

Sah, et al., "A Novel Method of Preparing PLGA Microcapsules Utilizing Methylethyl Ketone," Pharmaceutical Research, 13(3):360-367 (1996).

Sato, et al., "Porous Biodegradable Microspheres for Controlled Drug Delivery. I. Assessment of Processsing Conditions and Solvent Removal Techniques," Pharmaceutical Research, 5:(1): 21-30 (1988).

Szayna, M., et al., Exendin-4 Decelerates Food Intake, Weight Gain, and Fat Deposition in Zucker Rats, Endocrinology, 141(6):1936-1941 (2000).

Taylor, K. et al., Continuous Subcutaneous Infusion of AC2993 (Synthetic Exendin-4) Provides Sustained Day-Long Glycemic Control to Patients with Type 2 Diabetes, Diabetes, 51(Suppl 2):A85 (Jun. 2002 Conference Abstract).

Thomasin, et al., "A Contribution to Overcoming the Problem of Residual Solvents in Biodegradable Microspheres Prepared by Coacervation," Eur. J. Pharm. Biopharm. 42(1):16-24 (1996).

RESIDUAL SOLVENT EXTRACTION METHOD AND MICROPARTICLES PRODUCED THEREBY

BACKGROUND OF THE INVENTION

1. Field of the Invention

The present invention relates to preparation of microparticles containing an active agent. More particularly, the present invention relates to microparticles with a reduced level of residual solvent, and to a method for the preparation of such microparticles.

2. Related Art

Various methods are known by which compounds can be encapsulated in the form of microparticles. It is particularly advantageous to encapsulate a biologically active or pharmaceutically active agent within a biocompatible, biodegradable wall-forming material (e.g., a polymer) to provide sustained or delayed release of drugs or other active agents. In these methods, the material to be encapsulated (drugs or other active agents) is generally dissolved, dispersed, or emulsified in a solvent containing the wall forming material. Solvent is then removed from the microparticles to form the finished microparticle product.

An example of a conventional microencapsulation process is disclosed in U.S. Pat. No. 3,737,337 wherein a solution of a wall or shell forming polymeric material in a solvent is prepared. The solvent is only partially miscible in water. A solid or core material is dissolved or dispersed in the polymer-containing solution and, thereafter, the core-material-polymer-containing solution is dispersed in an aqueous liquid that is immiscible in the organic solvent.

Tice et al. in U.S. Pat. No. 4,389,330 describe the preparation of microparticles containing an active agent by using a two-step solvent removal process. In the Tice et al. process, the active agent and the polymer are dissolved in a solvent. The mixture of ingredients in the solvent is then emulsified in a continuous-phase processing medium that is immiscible with the solvent. A dispersion of microparticles containing the indicated ingredients is formed in the continuous-phase medium by mechanical agitation of the mixed materials. From this dispersion, the organic solvent can be partially removed in the first step of the solvent removal process. After the first stage, the dispersed microparticles are isolated from the continuous-phase processing medium by any convenient means of separation. Following the isolation, the remainder of the solvent in the microparticles is removed by extraction. After the remainder of the solvent has been removed from the microparticles, they are dried by exposure to air or by other conventional drying techniques.

Another conventional method of microencapsulating an agent to form a microencapsulated product is disclosed in U.S. Pat. No. 5,407,609. This method includes: (1) dissolving or otherwise dispersing one or more agents (liquids or solids) in a solvent containing one or more dissolved wall-forming materials or excipients (usually the wall-forming material or excipient is a polymer dissolved in a polymer solvent); (2) dispersing the agent/polymer-solvent mixture (the discontinuous phase) into a processing medium (the continuous phase which is preferably saturated with polymer solvent) to form an emulsion; and (3) transferring all of the emulsion immediately to a large volume of processing medium or other suitable extraction medium, to immediately extract the solvent from the microdroplets in the emulsion to form a microencapsulated product, such as microcapsules or microspheres.

U.S. Pat. No. 5,650,173 discloses a process for preparing biodegradable, biocompatible microparticles comprising a biodegradable, biocompatible polymeric binder and a biologically active agent, wherein a blend of at least two substantially non-toxic solvents, free of halogenated hydrocarbons, are used to dissolve both the agent and the polymer. The solvent blend containing the dissolved agent and polymer is dispersed in an aqueous solution to form droplets. The resulting emulsion is added to an aqueous extraction medium preferably containing at least one of the solvents of the blend, whereby the rate of extraction of each solvent is controlled, whereupon the biodegradable, biocompatible microparticles containing the biologically active agent are formed. Active agents suitable for encapsulation by this process include, but are not limited to, norethindrone, risperidone, and testosterone, and a preferred solvent blend is one comprising benzyl alcohol and ethyl acetate.

U.S. Pat. No. 5,654,008 describes a microencapsulation process that uses a static mixer. A first phase, comprising an active agent and a polymer, and a second phase are pumped through a static mixer into a quench liquid to form microparticles containing the active agent.

U.S. Pat. Nos. 5,792,477 and 5,916,598 ("the Rickey et al. patents") disclose a process whereby microparticles are contacted with an aqueous washing system to reduce the level of residual organic solvent to less than about 2% by weight of the microparticles. The aqueous washing system is water, or an aqueous solution of water and a solvent for the residual solvent in the microparticles. The aqueous washing system is at a temperature in the range of from about 25° C. to about 40° C. The organic solvent used in such a process is preferably a non-halogenated solvent, and most preferably benzyl alcohol alone or in combination with ethyl acetate.

Because the process disclosed in the Rickey et al. patents uses an aqueous washing system that reduces solvent levels, it suffers from the drawback that it may result in unacceptable depletion of water soluble active agents, such as peptides, from the microparticles.

The documents described above all disclose methods that can be used to prepare microparticles that contain an active agent. None of the documents described above solves the problem of removing residual solvent from microparticles containing a water soluble active agent, particularly when a halogenated solvent is used. None of the documents discussed above discloses a specific method for preparing microparticles that have lower residual solvent levels that is suitable for use with water soluble and non-water soluble active agents, as well as for halogenated solvents. Through the use of the non-aqueous washing system of the present invention, solvent levels can be significantly reduced to acceptable levels, while also maintaining acceptable levels of the active agent.

Thus, there is a need in the art for a method for preparing microparticles having low residual solvent levels for water soluble and non-water soluble active agents. There is a further need in the art for a non-aqueous washing system that can be used to reduce residual solvent levels, for halogenated solvents and non-halogenated solvents. The present invention, the description of which is fully set forth below, solves the need in the art for such methods and system.

SUMMARY OF THE INVENTION

The present invention relates to improved methods of preparing a pharmaceutical composition in microparticle form. In one aspect of the invention, the pharmaceutical composition is designed for the controlled release of an effective amount of an active agent over an extended period of time. The methods of the present invention may be carried out using pre-formed microparticles, or may additionally comprise the production of the microparticles. Particle formation may be effected by methods known to one skilled in the art, such as spray drying. More preferably, particle formation is effected by forming an emulsion, and removing solvent from the emulsion droplets to form microparticles. The invention also relates to the microparticles formed by the improved methods.

Viewed from a further aspect, the invention provides the use of microparticles prepared by the process of the invention for the manufacture of a medicament for use in a method of diagnosis or therapy.

Viewed from still a further aspect, the invention provides a method of treatment of the human or non-human animal body comprising the administration thereto of a composition according to the invention.

In one aspect of the present invention, a method for preparing microparticles is provided, which method comprises:
preparing an emulsion comprising an aqueous peptide solution and a biodegradable, biocompatible polymer dissolved in a halogenated solvent;
combining the emulsion with a coacervating agent that is free from solvents for the polymer to form a combined phase;
extracting the halogenated solvent from the combined phase with an extraction medium that is a non-solvent for the polymer and a solvent for the halogenated solvent and the coacervating agent, whereby microparticles precipitate out of the extraction medium; and
washing the precipitated microparticles in a non-aqueous washing system that is either (1) 100% ethanol or (2) a blend of ethanol and heptane to thereby reduce a level of residual halogenated solvent.

In another aspect of the present invention, a method for preparing microparticles is provided, which method comprises:
contacting microparticles comprising a biodegradable, biocompatible polymer matrix comprising a peptide and a halogenated solvent with a non-aqueous washing system to thereby reduce a level of residual halogenated solvent in the microparticles, wherein the washing system is either (1) 100% ethanol or (2) a blend of ethanol and heptane; and
recovering the microparticles from the washing system.

In yet another aspect of the present invention, the following method of preparing microparticles is provided:
contacting microparticles comprising a biodegradable, biocompatible polymer matrix comprising goserelin and a halogenated solvent with a non-aqueous washing system to thereby reduce a level of residual halogenated solvent to less than about 0.06% by weight of the microparticles, wherein the washing system is either (1) 100% ethanol or (2) a blend of ethanol and heptane; and
recovering the microparticles from the washing system.

In still another aspect of the present invention, a method for preparing microparticles is provided, which method comprises:
preparing a first phase comprising a biodegradable, biocompatible polymer and a halogenated solvent;
preparing an aqueous second phase comprising a peptide;
combining the first phase and the second phase under the influence of a mixer to form an emulsion;
combining the emulsion with a coacervating agent that is free from solvents for the polymer to form a combined phase;
extracting the halogenated solvent from the combined phase with an extraction medium that is a non-solvent for the polymer and a solvent for the halogenated solvent and the coacervating agent, whereby microparticles precipitate out of the extraction medium; and
washing the precipitated microparticles in a non-aqueous washing system that is either (1) 100% ethanol or (2) a blend of ethanol and heptane to thereby reduce a level of residual halogenated solvent.

In a further aspect of the present invention, a method is provided which comprises:
preparing an emulsion comprising an aqueous peptide solution and a biodegradable, biocompatible polymer dissolved in a halogenated solvent;
combining the emulsion with a coacervating agent that is free from solvents for the polymer to form a combined phase;
extracting the halogenated solvent from the combined phase with an extraction medium that is a non-solvent for the polymer and a solvent for the halogenated solvent and the coacervating agent, whereby microparticles precipitate out of the extraction medium; and
washing the precipitated microparticles in a non-aqueous washing system that comprises ethanol.

Another aspect of the present invention includes a method for preparing microparticles, which method comprises:
contacting microparticles comprising a biodegradable, biocompatible polymer matrix containing an active agent and an organic solvent with a non-aqueous washing system to thereby reduce the level of residual organic solvent in the microparticles, wherein the non-aqueous washing system is either (1) 100% ethanol or (2) a blend of ethanol and heptane; and
recovering the microparticles from the non-aqueous washing system.

In a further aspect of the present invention, a method for preparing microparticles comprises:
preparing a first phase, the first phase comprising an active agent, a biodegradable, biocompatible polymer, and a solvent;
preparing a second phase, wherein the first phase is substantially immiscible with the second phase;
combining the first phase and the second phase to form an emulsion;
extracting solvent from the emulsion using an extraction liquid to thereby form microparticles containing the active agent; and
washing the microparticles with a non-aqueous washing system to thereby reduce the level of residual solvent in the microparticles, wherein the non-aqueous washing system comprises ethanol.

In yet a further aspect of the present invention, a method for preparing microparticles comprises:
preparing an emulsion comprising an aqueous peptide solution and a biodegradable, biocompatible polymer dissolved in a solvent;
combining the emulsion with a coacervating agent that is free from solvents for the polymer to form a combined phase;
extracting solvent from the combined phase in an extraction medium that is a non-solvent for the polymer and a solvent for the solvent and the coacervating agent, whereby microparticles precipitate out of the extraction medium; and
washing the precipitated microparticles in 100% ethanol.

In other aspects of the present invention, the peptide is a luteinizing-hormone-releasing-hormone (LHRH) analogue.

One such LHRH analogue is goserelin. In further aspects of the invention the blend is a 3:1 ratio of ethanol to heptane, or a 1:1 ratio of ethanol to heptane. In other aspects of the present invention, the active agent is risperidone, 9-hydroxyrisperidone, or pharmaceutically acceptable salts thereof. In other aspects of the invention, the solvent is a solvent blend of benzyl alcohol and ethyl acetate. Still further aspects of the present invention include microparticles prepared by any of the above methods.

In still a further aspect of the present invention, a method for preparing microparticles is provided which comprises:
  preparing an emulsion comprising an active agent and a biodegradable, biocompatible polymer dissolved in a solvent;
  combining the emulsion with a coacervating agent that is free from solvents for the polymer to form a combined phase; and
  extracting the solvent from the combined phase with a solvent blend of a hardening solvent and a washing solvent, to thereby form hardened microparticles.

In further aspects of such a method, the hardening solvent is a liquid alkane, such as heptane, and the washing solvent is an alcohol, such as ethanol. Such a method may also include, after the extracting step, a step of rinsing the microparticles with the hardening solvent.

FEATURES AND ADVANTAGES

The present invention advantageously can be used for water soluble active agents, such as peptides, and non-water soluble active agents such as risperidone.

Another advantage of the present invention is that it can be used to reduce levels of residual solvents to an acceptable level for parenteral injection. The present invention is particularly advantageous in reducing residual levels of halogenated solvents.

By reducing the levels of residual solvents, the present invention advantageously provides a safer product with lower potential toxicity. Moreover, the reduced levels of residual solvents achieved by the present invention result in improved handling properties of this microsphere and extend the shelf life of the product.

The present invention also advantageously provides a method whereby hardening and washing of the microparticles can be accomplished in a single step through use of a solvent blend.

BRIEF DESCRIPTION OF THE FIGURES

The present invention is described with reference to the accompanying drawings. In the drawings, like reference numbers indicate identical or functionally similar elements. Additionally, the left-most digit of a reference number identifies the drawing in which the reference number first appears.

DETAILED DESCRIPTION OF THE PREFERRED EMBODIMENTS

Overview

Figure 1:
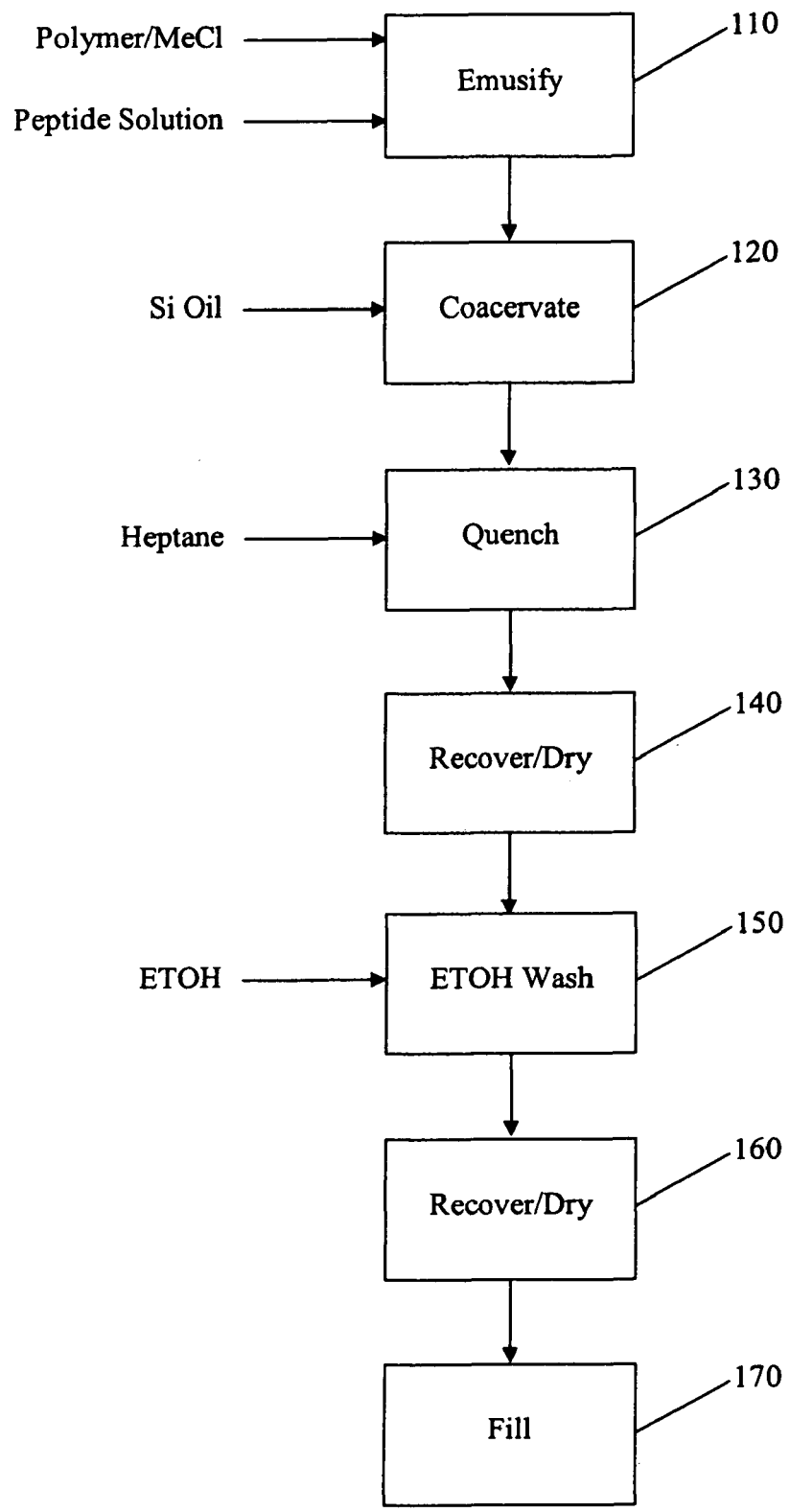
FIG. 1 shows one embodiment of a process for making microparticles in accordance with the present invention.

The present invention relates to microparticles that contain an active agent, and methods for preparing such microparticles. The present invention provides a method for preparing microparticles, which have lower residual solvent levels, that is suitable for use with water-soluble and non-water soluble active agents, as well as for use with halogenated solvents. Through the use of the non-aqueous washing system of the present invention, solvent levels can be significantly reduced to acceptable levels, while also maintaining acceptable levels of the active agent.

In one embodiment of the present invention, a washing process is carried out on the microparticles. The washing process is carried out on a finished microparticle product, prior to any filling operation. It should be readily apparent to one skilled in the art, that the present invention is not limited to any particular method of preparing a finished microparticle product. For example, finished microparticles can be prepared using emulsion-based methods of preparing microparticles. Suitable emulsion-based methods that can be used to prepare finished microparticles include phase separation methods that use a coacervating agent. Other suitable emulsion-based methods include non-phase separation methods that use other means for extracting solvent to form hardened microparticles. Suitable methods of preparing a finished microparticle product are disclosed in, for example, the following U.S. patents, the entirety of each of which is incorporated herein by reference: U.S. Pat. Nos. 3,737,337; 4,389,330; 5,407,609; 5,650,173; 5,654,008; 5,792,477; 5,916,598; 5,945,126; and 6,110,503.

In one preferred embodiment of the present invention, the microparticles are made using an emulsion-based process. In such a preferred embodiment, the method of the present invention includes preparing an emulsion that comprises a first phase and a second phase. The first phase preferably comprises an active agent, a polymer, and a solvent for the polymer. The second phase is a continuous phase, preferably an aqueous phase. The solvent is extracted from the emulsion to form microparticles containing the active agent. The microparticles are contacted with a non-aqueous washing system to reduce the level of any halogenated solvent to less than about 0.06% by weight of the microparticles. Preferably, the non-aqueous washing system is either 100% ethanol, or a blend of ethanol and heptane.

To ensure clarity of the description that follows, the following definitions are provided. By "washing system" or "washing solvent" is meant a solvent or solvent system that functions to facilitate extraction of polymer and/or active agent solvents, coacervating agents, and the like from the microparticles. By "hardening solvent" is meant a solvent that functions to harden coacervates into microparticles. The process of hardening microparticles may be referred to herein as a "quench" process. By "halogenated solvent" is meant halogenated organic solvents, i.e., $C_1$-$C_4$ halogenated alkanes, e.g., methylene chloride, chloroform, methyl chloride, carbon tetrachloride, ethylene dichloride, ethylene chloride, 2,2,2-trichloroethane, and the like. By "microparticles" or "microspheres" is meant solid particles that contain an active agent or other substance dispersed or dissolved within a polymer that serves as a matrix or binder of the particle. The polymer is preferably biodegradable and biocompatible. By "biodegradable" is meant a material that should degrade by bodily processes to products readily disposable by the body and should not accumulate in the body. The products of the biodegradation should also be biocompatible with the body. By "biocompatible" is meant not toxic to the body, is pharmaceutically acceptable, is not carcinogenic, and does not significantly induce inflammation in body tissues. As used herein, "body" preferably refers to the human body, but it should be understood that body can also refer to a non-human animal body. By "weight %" or "% by weight" is meant parts by weight per hundred parts total weight of microparticle. For example, 10 wt. % active agent would mean 10 parts active agent by weight and 90 parts polymer by weight. Unless otherwise indicated to the contrary, percentages (%) reported herein are by weight. By "controlled release microparticle" or "sustained release microparticle" is meant a microparticle from which an active agent or other type of substance is released as a function of time. By "mass median diameter" is meant the diameter at which half of the distribution (volume percent) has a larger diameter and half has a smaller diameter.

Methods of the Present Invention

Turning now to FIG. 1, one embodiment of a process of the present invention for making microparticles is shown. In such a process, a polymer solution is formed by dissolving the polymer in a polymer solvent such as methylene chloride ($CH_2Cl_2$, referred to herein as "MeCl"). Solvents for the polymer will vary depending upon, for example, the nature of the polymer, the active agent, and compatibility with other solvents being used. It should be readily apparent to one skilled in the art that the present invention is not limited to the use of MeCl or to the use of halogenated solvents. Selection of a suitable solvent would be readily apparent to one skilled in the art. The polymer is preferably a biodegradable, biocompatible polymer, such as poly(glycolic acid), poly(d,l-lactic acid), poly(l-lactic acid), copolymers of the foregoing, and the like. Preferred polymers include poly(lactide-co-glycolide) materials (PLGA). Solvents suitable for such polymers include MeCl, chloroform, ethyl acetate, substituted pyrrolidone, and the like. It should be readily apparent to one skilled in the art that the present invention is not limited to a particular polymer. Other suitable polymers include, for example, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, polyphosphazines, and natural polymers including albumin, casein, and waxes, such as glycerol mono- and distearate, and the like.

In a step 110, an aqueous peptide solution is emulsified with the polymer solution to form an emulsion (W/O emulsion). Peptides suitable for use with the present invention include, but are not limited to, luteinizing-hormone-releasing hormone (LHRH) analogues, such as goserelin.

In a step 120, silicone oil is added to the emulsion as a coacervating agent to form a combined phase. Silicone (polydimethylsiloxane) is an incompatible polymer to PLGA, and acts to extract methylene chloride from the polymer solution. As would be readily apparent to one skilled in the art, other suitable coacervating agents could be used depending upon the polymer and solvent. After addition of a small volume of silicone oil, embryonic microparticles form. Once the microparticles form, the combined phase is transferred in a step 130 to an extraction or quench tank that contains an extraction or quench medium such as heptane. Heptane is a non-solvent to the polymer, but is a good solvent for both the polymer solvent methylene chloride and the coacervating agent silicone oil. It should be understood that the present invention is not limited to use of heptane as an extraction medium. As would be readily apparent to one skilled in the art, other extraction media can be used. Preferably, the extraction medium is a non-solvent for the polymer being used, but a solvent for both the polymer solvent and coacervating agent being used. Microparticles precipitate out of the extraction medium. In a step 140, the precipitated microparticles are recovered, and optionally dried in a manner known to one skilled in the art.

The microparticles recovered in step 140 have residual solvent levels of methylene chloride, a halogenated solvent, that are unacceptably high, in excess of approximately 1%. International guidelines for parenteral materials (ICH Guidelines) require a maximum MeCl level of 0.06%. In order to reduce the level of residual solvent, a washing step 150 is carried out with a non-aqueous washing system. In one embodiment of the present invention, the non-aqueous washing system is 100% of an alcohol, preferably ethanol. Other suitable alcohols include, but are not limited to, methanol, 2-propanol, and isopropanol. In an alternative embodiment of the present invention, the non-aqueous washing system is a blend of an alcohol and a liquid alkane. Suitable liquid alkanes include, but are not limited to, pentane, hexane, and heptane. In a preferred embodiment of the present invention, the non-aqueous washing system is a blend of ethanol and heptane. Washing step 150 is carried out to reduce the level of residual solvent in the microparticles. Preferably, washing step 150 is carried out until the level of MeCl, or other halogenated solvent in the microparticles, is less than about 0.06% by weight. Thereafter, the microparticles are recovered and dried in a manner known to one skilled in the art, as shown in a step 160. The microparticles can then be filled into vials for storage and use, as shown in a step 170.

The non-aqueous washing system of the present invention is preferred over conventional aqueous washing solutions, such as those disclosed in U.S. Pat. No. 5,792,477. Although aqueous washing solutions may reduce solvent levels, they result in unacceptable depletion of the peptide from the microparticles. Through the use of the non-aqueous washing system of the present invention, solvent levels can be significantly reduced to acceptable levels, while also maintaining acceptable levels of the peptide.

Example 1

Microparticles were prepared in accordance with the phase separation method described above and shown in FIG. 1. The polymer solution was prepared by dissolving 2.7144 g 65:35 poly(d,l-lactic-co-glycolic acid), MEDISORB® 6535 DL 2M polymer, approximately 20 kD molecular weight (Alkermes, Inc.) in 40.2 g methylene chloride. An approximate 30 wt % aqueous goserelin solution was prepared by dissolving 339.9 mg goserelin containing 82.8% peptide content (Polypeptide Laboratories) in 0.816 g deionized water. The polymer and goserelin solutions were mixed and probe sonicated for 20 seconds to form a water-in-oil emulsion. The emulsion was added to a 250-ml glass reactor. The stir speed was 1000 RPM. The polymeric precipitant, 350 centistoke silicone oil (Dow Corning) was slowly added by peristaltic pump to the reactor to induce phase separation. Addition was discontinued after adding a total of 62.2 g (1.5 to 1 ratio of silicone oil to methylene chloride) over a time period of approximately 5 minutes. The embryonic microparticles were gravity transferred into a 3 liter heptane quench at 22° C. After about 3 hours in the heptane quench, the microparticles were harvested by vacuum filtration and dried overnight under vacuum. The theoretical loading of the microparticles was 9.5 wt %.

After completion of the recovery and drying step 140, samples of the goserelin microparticles were subjected to various washing treatments or process stages as shown in step 150. The processing stages included a control (no washing), and washing with the following washing systems for a period of about two hours: water at 0° C.; water at 30° C.; 100% ethanol at 30° C.; 100% ethanol at 0° C.; 50% ethanol/50% water at 15° C. After the washing treatment, the microparticles were recovered and dried. The residual solvent levels (GC), and the goserelin content (HPLC), were measured for the dried microparticles, as shown below in Table 1.

TABLE 1

| Sample No. | Process Stage | Heptane Wt % | MeCl Wt % | Ethanol Wt % | Goserelin Content % |
|---|---|---|---|---|---|
| 1 | Control | 2.3 | 1.0 | N/A | 7.8 |
| 2 | Water 30° C. | 1.6 | ND[1] | N/A | 2.3 |
| 3 | Water 0° C. | 2.0 | 0.2 | N/A | 5.0 |
| 4 | 100% Ethanol 30° C. | 0.004 | ND[1] | 2.7 | 8.0 |
| 5 | 100% Ethanol 0° C. | 1.7 | 0.3 | 0.05 | 6.7 |
| 6 | 50% Ethanol/ 50% Water 15° C. | 0.1 | ND[1] | 0.03 | 4.3 |

[1]ND: None detected. Below detection threshold level of 0.01%

As can be seen from Table 1, the control with sample 1 resulted in high levels of goserelin content, but unacceptably high levels of residual solvent, particularly MeCl. The aqueous washing systems used with samples 2, 3, and 6 resulted in significant depletion of goserelin content, although they were effective in reducing the levels of residual solvents. The non-aqueous washing system used with samples 4 and 5 reduced the residual solvent levels, while maintaining the levels of goserelin content. The 100% ethanol washing system at 30° C. resulted in the highest level of goserelin content, with below detectable levels of MeCl. Since "none detected" is less than 0.01 wt. %, such microparticles would meet the ICH guidelines for parenteral materials.

Example 2

Further experiments were done to determine the effect of temperature on solvent extraction using 100% ethanol. Microparticles were prepared in accordance with the method described above for Example 1. After completion of the recovery and drying step 140, samples of the goserelin microparticles were subjected to various washing treatments as shown in step 150. The process stages included a control (no washing), and washing with the following washing systems for a period of about two hours: 100% ethanol at 10° C.; 100% ethanol at 21° C.; and 100% ethanol at 26° C. After the washing treatment, the microparticles were recovered and dried. The residual solvent levels (GC), and the goserelin content (HPLC), were measured for the dried microparticles, as shown below in Table 2.

TABLE 2

| Sample No. | Process Stage | Heptane Wt % | MeCl Wt % | Ethanol Wt % | Goserelin Content % |
|---|---|---|---|---|---|
| 1 | Control | 2.5 | 1.5 | N/A | 6.3 |
| 2 | 100% Ethanol 10° C. | 2.3 | 1.2 | 0.1 | 5.9 |
| 3 | 100% Ethanol 21° C. | 0.1 | 0.08 | 0.2 | 5.8 |
| 4 | 100% Ethanol 26° C. | 0.006 | 0.05 | 3.5 | 6.4 |

As can be seen from Table 2, the temperature had little effect on the goserelin content, and a significant effect on the residual solvent levels. At a temperature of 26° C., the goserelin content remained high, with a residual solvent level of MeCl of 0.05 wt. %.

Example 3

Three separate samples of microparticles were prepared in accordance with the method described above for Example 1. The microparticles were recovered from the extraction tank containing heptane in step 140, but were not dried. Without drying, sample 1 was placed immediately into 100% ethanol. For samples 2 and 3, the microparticles were allowed to settle in the extraction tank. Because of the low specific gravity of heptane, the microparticles settle quickly. For sample 2, a portion of the heptane was decanted and ethanol added to result in a 3:1 ratio of ethanol to remaining heptane. For sample 3, a portion of the heptane was decanted and ethanol added to result in a 1:1 ratio of ethanol to remaining heptane. The washing treatment for samples 1, 2, and 3 was carried out at 20° C. for a period of about two hours. After the washing treatment, the microparticles were recovered and dried. The residual solvent levels (GC), and the goserelin content (HPLC), were measured for the dried microparticles, as shown below in Table 3.

TABLE 3

| Sample No. | Process Stage | Heptane Wt % | MeCl Wt % | Ethanol Wt % | Goserelin Content % |
|---|---|---|---|---|---|
| 1 | 100% Ethanol | 0.9 | 0.1 | 1.3 | 6.9 |
| 2 | 3:1 Ethanol to Heptane | 1.8 | 0.07 | 1.1 | 7.0 |
| 3 | 1:1 Ethanol to Heptane | 2.3 | 0.2 | 1.0 | 6.9 |

As can be seen from Table 3, a washing system using ethanol and heptane maintained the levels of goserelin content while significantly reducing the residual solvent levels.

Example 4

Further experiments were done to determine the effect of wash time on solvent extraction using 100% ethanol. A six-gram batch of 9.5% theoretically loaded goserelin microparticles was prepared in accordance with the method described above for Example 1. The microparticles were recovered from the extraction tank containing heptane in step 140, but were not dried. Samples of the goserelin microparticles were subjected to various washing treatments as shown in step 150. The process stages included a control (no washing), and washing with 100% ethanol at 15° C. for periods of 15, 30, 60, 90, and 120 minutes. After the washing treatment, the microparticles were recovered and dried. The residual solvent levels (GC) and the goserelin content (HPLC), were measured for the dried microparticles, as shown below in Table 4.

TABLE 4

| Sample No. | Process Stage | Heptane Wt % | MeCl Wt % | Ethanol Wt % | Goserelin Content % |
|---|---|---|---|---|---|
| 1 | Control | 2.4 | 1.3 | N/A | 7.4 |
| 2 | 15 min. Wash | 0.7 | 0.2 | 3.9 | 7.3 |
| 3 | 30 min. Wash | 0.4 | 0.045 | 4.6 | 7.3 |
| 4 | 60 min. Wash | 0.4 | ND[1] | 4.6 | 7.5 |
| 5 | 90 min. Wash | 0.3 | ND | 5.1 | 6.8 |
| 6 | 120 min. Wash | 0.3 | ND | 5.0 | 6.9 |
| 7 | Final Product | 0.8 | 0.012 | 0.4 | 6.4 |

[1]ND: None detected. Below detection threshold level of 0.01%.

As can be seen from Table 4, residual levels of MeCl decrease rapidly and reach the target of 0.06% between 15 and 30 minutes. Goserelin levels are maintained for about 60 minutes and then decline slightly.

Example 5

A 50 gram batch of 5% theoretically loaded BSA microparticles was prepared by a phase separation process. The polymer solution was prepared by dissolving 45.5 g 65:35 poly(d,l-lactic-co-glycolic acid), MEDISORB® 6535 DL 2M polymer, approximately 20 kD molecular weight (Alkermes, Inc.) in 698.0 g methylene chloride. An aqueous bovine serum albumin (BSA) solution was prepared by dissolving 2.48 g BSA in 13.5 g deionized water. The polymer and BSA solutions were mixed and probe sonicated for 1 minute to establish a water-in-oil emulsion. The emulsion was added to a 2 liter glass reactor. The stir speed was set to 1000 RPM. The polymeric precipitant, 350 centistoke silicone oil (Dow Corning) was slowly added to the reactor to induce phase separation. Addition was discontinued after adding a total of 1032 g over a time period of approximately 8 minutes. The amount of silicone oil was approximately a 1.5 to 1 ratio of silicone oil to methylene chloride. The embryonic microparticles were gravity transferred into a 10 gallon heptane quench at about 3° C. After about 2 hours in the heptane quench, the microparticles were collected onto a cone filter containing a 25 micron stainless steel mesh. The microparticles were backflushed into the quench tank with 14.3 kg ethanol. The jacket temperature was increased to about 15° C. and stirred for 5 hours. Samples of the microparticle/ethanol slurry were taken, dried overnight, and analyzed for residual solvent levels (GC).

Processing stages included a control (no washing), and washing with 100% ethanol at 15° C. for periods of 0.5, 1, 2, and 3 hours (samples 2-5, respectively). As can be seen from the residual solvent levels shown below in Table 5, a wash time of greater than about one hour resulted in residual solvent levels of MeCl of about 0.01 wt %, significantly less than about 0.06 wt %.

Samples 6-9 in Table 5 were all subjected to the 3 hour ETOH wash. Samples 6-9 were then dried, using either a nitrogen purge or a vacuum dry as shown in Table 5. The additional drying regimen did not appear to have any effect on the residual levels of heptane or MeCl.

TABLE 5

| Sample No. | Process Stage | Heptane Wt % | MeCl Wt % | Ethanol Wt % |
|---|---|---|---|---|
| 1 | Control | 2.2 | 1.5 | N/A |
| 2 | 0.5 hr. ETOH Wash | 1.5 | 0.1 | 0.005 |
| 3 | 1.0 hr. ETOH Wash | 1.0 | 0.012 | 0.10 |
| 4 | 2.0 hr. ETOH Wash | 0.5 | ND[1] | 0.01 |

TABLE 5-continued

| Sample No. | Process Stage | Heptane Wt % | MeCl Wt % | Ethanol Wt % |
|---|---|---|---|---|
| 5 | 3.0 hr. ETOH Wash | 0.4 | ND | 0.02 |
| 6 | 18 hr. Nitrogen Purge | 0.4 | ND | 0.20 |
| 7 | 18 hr. Vacuum Dry | 0.4 | ND | 0.18 |
| 8 | 42 hr. Nitrogen Purge | 0.4 | ND | 0.20 |
| 9 | 42 hr. Vacuum Dry | 0.4 | ND | 0.02 |

[1]ND: None detected. Below detection threshold level of 0.01%.

Example 6

A 50 gram batch of 5% theoretically loaded BSA microparticles was prepared in the manner described above in Example 5. However, the ethanol wash temperature was 20° C. Samples 1 through 3 (shown below in Table 6) were taken after 30 minutes, 1 hour, and 2 hours, respectively, in the heptane quench, and were not subjected to a washing treatment. Samples 4 through 8 were subjected to the 100% ethanol washing system at 20° C. for 45 minutes, 1.5 hours, 3 hours, 4 hours, and 5 hours, respectively. As can be seen from the residual solvent levels shown below in Table 6, increasing the wash time from about 45 minutes to about 1.5 hours reduced the residual solvent level of MeCl from 0.2 wt % to none detected.

TABLE 6

| Sample No. | Process Stage | Heptane Wt % | MeCl Wt % | Ethanol Wt % |
|---|---|---|---|---|
| 1 | 30 min. Quench | 2.5 | 3.3 | N/A |
| 2 | 1 hr. Quench | 2.4 | 3.3 | N/A |
| 3 | 2 hr. Quench | 2.4 | 3.4 | N/A |
| 4 | 45 min. Wash | 1.8 | 0.2 | 2.9 |
| 5 | 1.5 hr. Wash | 0.6 | ND[1] | 3.3 |
| 6 | 3.0 hr. Wash | 0.4 | ND | 3.5 |
| 7 | 4.0 hr. Wash | 0.3 | ND | 4.5 |
| 8 | 5.0 hr. Wash | 0.2 | ND | 5.8 |

[1]ND: None detected. Below detection threshold level of 0.01%.

Figure 2:
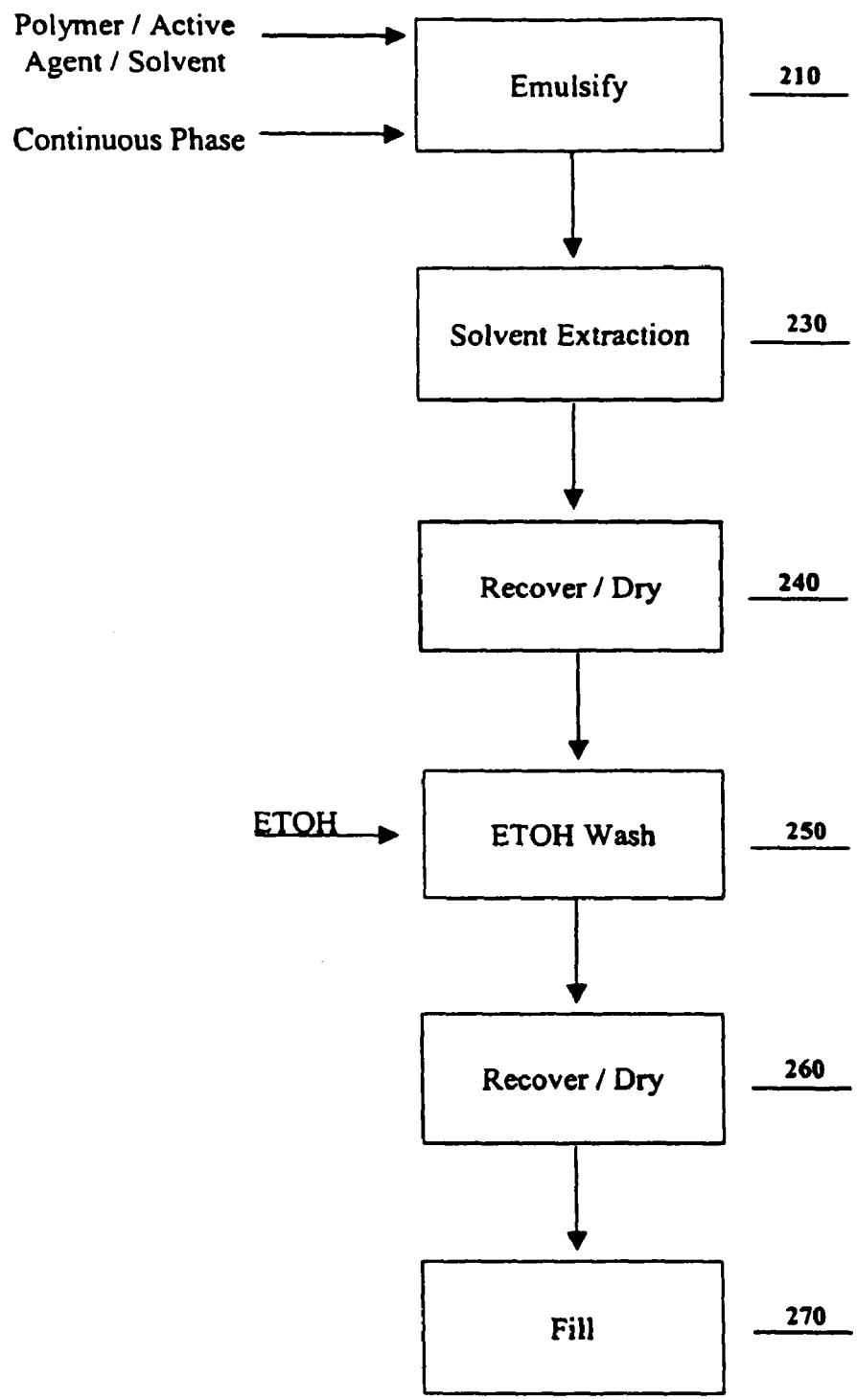
FIG. 2 shows another embodiment of a process for making microparticles in accordance with the present invention.

Turning now to FIG. 2, another embodiment of a process of the present invention for making microparticles is shown. In such a process, a first phase is prepared that comprises an active agent, a polymer, and a solvent. The polymer is preferably a biodegradable, biocompatible polymer, such as poly (glycolic acid), poly(d,l-lactic acid), poly(l-lactic acid), copolymers of the foregoing, and the like. Preferred polymers include poly(lactide-co-glycolide) materials (PLGA). The solvent is preferably a solvent for the polymer. The solvent may also be a solvent for the active agent. Alternatively, the active agent is dispersed, rather than dissolved, in the first phase. In yet another alternative embodiment, a first solvent is used for the polymer, and a second solvent is used for the active agent. In such an embodiment, the polymer solution and the active agent solution are combined to form the first phase. A second continuous phase is prepared. The first phase is substantially immiscible with the second phase. The first and second phases are combined in a step 210 to form an emulsion. Step 210 can be carried out, for example, by combining the first and second phases in a mixer such as a static mixer.

In a step 230, solvent is extracted from the emulsion. In one embodiment of the present invention, solvent is extracted using an extraction liquid to extract solvent from the emulsion, thereby hardening the emulsion droplets to form microparticles that contain the active agent. Such solvent extraction can be carried out, for example, in a tank containing the extraction liquid. In a step 240, the hardened microparticles are recovered, and optionally dried in a manner known to one skilled in the art.

In order to further reduce the level of residual solvents in the microparticles, a washing step 250 is carried out with a non-aqueous washing system. In one embodiment of the present invention, the non-aqueous washing system is an alcohol, preferably 100% ethanol. In an alternative embodiment of the present invention, the non-aqueous washing system is a blend of an alcohol and a liquid alkane, preferably ethanol and heptane. Washing step 250 is carried out to reduce the level of residual solvent in the microparticles. Preferably, washing step 250 is carried out until the level of residual solvent in the microparticles is reduced to acceptable levels. Thereafter, the microparticles are recovered and dried in a manner known to one skilled in the art, as shown in a step 260. The microparticles can then be filled into vials for storage and use, as shown in a step 270.

Example 7

Microparticles containing risperidone were prepared at the one-kilogram scale in accordance with the method described above and shown in FIG. 2. The 1 Kg process (400 grams of active agent and 600 grams of polymer) provides a theoretical drug loading of the microparticles of 40%.

A 16.7 wt. % polymer solution was prepared by dissolving 600 grams of 90:10 poly (d,l-lactic-co-glycolic acid), MEDISORB® 9010 DL, approximate molecular weight of 100-120 kD (Alkermes, Inc.) in ethyl acetate (EtAc). A 24 wt. % drug solution was prepared by dissolving 400 grams of risperidone (Janssen Pharmaceutica, Beerse, Belgium) in benzyl alcohol (BA). An active agent/polymer solution (organic phase) was prepared by mixing the drug solution into the polymer solution. The active agent/polymer solution was maintained at a temperature of 25±5° C.

The second, continuous phase was prepared by preparing a 30 liter solution of 1% PVA, the PVA acting as an emulsifier. To this was added 2086 grams of ethyl acetate to form a 6.5 wt. % solution of ethyl acetate. The two phases were combined using a static mixer, such as a 1″ Kenics static mixer available from Chemineer, Inc., North Andover, Mass., to form an emulsion as shown in step 210.

The emulsion was transferred to a solvent extraction medium, as in step 230. The solvent extraction medium was 2.5% solution of ethyl acetate and water-for-injection (WFI) at 5-10° C. The volume of the solvent extraction medium is 0.25 L per gram of batch size.

After completion of the solvent extraction step, the microparticles were collected, de-watered, and dried, as in step 240. The temperature was maintained at less than about 15° C.

After completion of the recovery and drying step 240, samples of the risperidone microparticles were subjected to various process stages or washing treatments as shown in step 250. The process stages included a control (no washing), and washing with the following washing systems for a period of about six hours: 100% ethanol at ambient temperature (20° C.); 100% ethanol at 4° C.; and 100% ethanol at 10° C. After the washing treatment, the microparticles were collected onto a 25 µm screen, rinsed with cold WFI, and dried to form finished microparticles. The residual solvent levels (GC), and the risperidone content (HPLC), were measured for the finished microparticles, as shown below in Table 7.

TABLE 7

| Sample No. | Process Stage | BA Wt % | Ethanol Wt % | EtAc Wt % | Risperidone Content |
|---|---|---|---|---|---|
| 1 | Control | 4.53 | 0.3 | 2.73 | 34.9 |
| 2 | 100% Ethanol Ambient | 0.07 | 0.04 | 0.00 | 21.7 |
| 3 | 100% Ethanol 10° C. | 0.13 | 0.03 | 0.02 | 26.1 |
| 4 | 100% Ethanol 4° C. | 0.20 | 0.00 | 0.02 | 23.2 |

The finished microparticles for samples 1-3 were free flowing powders, indicating that the level of residual solvents, particularly benzyl alcohol, had been reduced to acceptable levels for a useful product. Preferably, the level of residual processing solvents is individually reduced to a level in the range of from about 0.2 to about 2.0 wt. %. As can be seen from Table 7, the 100% ethanol washing system of the present invention significantly reduced the individual residual solvent level to less than about 0.2 wt. %, while maintaining the risperidone content at an acceptable level.

Figure 3:
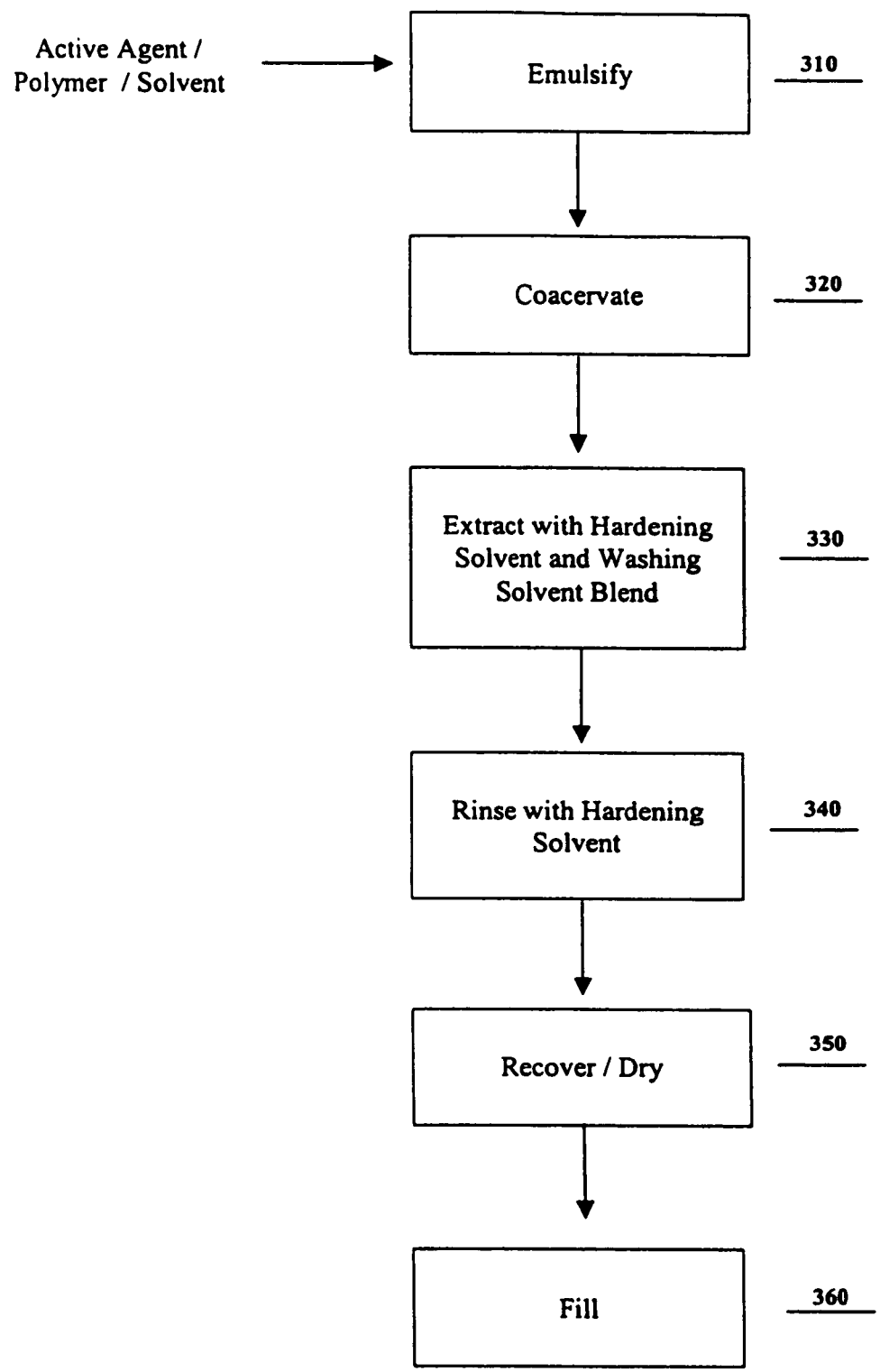
FIG. 3 shows a further embodiment of a process for making microparticles in accordance with the present invention.

Turning now to FIG. 3, another embodiment of a process of the present invention for making microparticles is shown. In such a process, an active agent is dispersed or dissolved in an aqueous medium. The aqueous solution is mixed with an organic solvent in which is dissolved a polymer, resulting in a water-in-oil (W/O) emulsion. The polymer is preferably a biodegradable, biocompatible polymer, such as poly(glycolic acid), poly(d,l-lactic acid), poly(l-lactic acid), copolymers of the foregoing, and the like. Preferred polymers include poly(lactide-co-glycolide) materials (PLGA). The aqueous solution and the polymer solution are combined in a step 310 to form an emulsion. Step 310 can be carried out, for example, by combining the two solutions in a mixer such as a static mixer. Alternatively, step 310 can be carried out using suitable emulsion techniques such as sonication or homogenization.

In a step 320, a coacervating agent is added to the emulsion, preferably with continuous stirring. The coacervating agent is preferably a non-solvent for the polymer. Suitable coacervating agents include, but are not limited to, dimethicone and silicone oil. The polymer precipitates to encapsulate the active agent to form coacervates or embryonic microparticles.

In a step 330, the dispersion of coacervates is added to a solvent blend that includes a hardening solvent and a washing solvent. The solvent blend extracts polymer solvent and the coacervating agent from the coacervates, to thereby form hardened microparticles. The solvent blend is a physical blend of two types of solvents: a hardening solvent that is used to harden the coacervates into microparticles; and a washing solvent that is used to facilitate extraction of polymer solvent and coacervating agent from the microparticles. Suitable hardening solvents include, but are not limited to, heptane, hexane, cyclohexane, diethyl ether, petroleum ether, mineral oil, fatty acid esters, and caprylate triglyceride. Suitable washing solvents include, but are not limited to, ethanol and isopropanol. In a preferred embodiment of the present invention, the hardening solvent is a liquid alkane, and the washing solvent is an alcohol. In an alternate preferred embodiment, the hardening solvent is heptane and the washing solvent is ethanol. In further embodiments, the solvent blend is made up of 90% heptane and 10% ethanol, and 95% heptane and 5% ethanol. Preferably, the solvent blend is made up of from about 50% heptane and about 50% ethanol to about 95% heptane and about 5% ethanol.

In one embodiment of the method shown in FIG. 3, a step 340 is carried out after step 330 to rinse the microparticles with a hardening solvent. The hardening solvent used in step 340 may be the same as, or different from, the hardening solvent used in step 330. The volume of hardening solvent used in step 340 is preferably equal to or less than the volume of the solvent blend used in step 330. Step 340 may be carried out to ensure complete hardening of the microparticles.

In a step 350, the hardened microparticles are recovered, and optionally dried in a manner known to one skilled in the art. The microparticles can then be filled into vials for storage and use, as shown in a step 360. In an alternate embodiment of the present invention, step 340 is eliminated, and the microparticles are recovered and optionally dried in step 350 after step 330.

Example 8

Microparticles were prepared in accordance with the method described above and shown in FIG. 3. The polymer solution was prepared by dissolving 9.8 g 50:50 poly(d,l-lactic-co-glycolic acid), MEDISORB® 5050DL 4A polymer, approximate molecular weight of 50 kD (Alkermes, Inc.) in methylene chloride in an Erlenmeyer flask. About 100 mg of sucrose was dissolved in 2 g of water for injection at room temperature in a scintillation vial. The sucrose solution was added to the polymer solution and sonicated using a probe sonicator at 40% amplitude for 1 minute duration. The sonication was repeated 3 times with a 3 minute gap in between. The resulting emulsion was transferred into a 500 ml reactor and stirred at 907 rpm using an impeller. 225 g of dimethicone (350 centistoke) was added using a glass syringe and funnel over a period of 20 minutes. The coacervate dispersion was transferred into 3 different beakers containing 1000 g of the following solvents: 100% heptane (Batch 1A); 90% heptane/10% ethanol (Batch 1B); and 50% heptane/50% ethanol (Batch 1C).

The solvents were kept in an ice bath (2.2 to 2.5° C.) and stirred for about 60 minutes. The suspension was allowed to settle down and the solvents were decanted. 1000 g of fresh heptane was added to each of the beakers, and stirred for 30 minutes. The microparticles were collected using vacuum filtration. The collected microparticles were transferred to petri-dish and allowed to dry at room temperature overnight.

Two additional batches (2A and 2B) were prepared using the process described above for Batches 1A-1C. After the sonication step described above, the emulsion was transferred to a 500 ml reactor. With continuous stirring at 1630 rpm, 225 g of dimethicone (1000 centistoke) was slowly added to the reactor using a peristaltic pump. The coacervate dispersion was transferred to 2 separate beakers each containing 1000 g of heptane (Batch 2A) and 90% heptane/10% ethanol (Batch 2B) respectively. After 60 minutes of mixing, the solvent was decanted and the microparticles were further hardened with 500 g of fresh heptane. The products were recovered and dried in a static cone dryer.

The residual solvent levels for Batches 1A-1C and 2A-2B are shown below in Table 8. As shown in Table 8, the 90% heptane/10% ethanol and 50% heptane/50% ethanol solvent combinations produced microparticles with lower levels of methylene chloride (e.g., reduction improvement of 48% to 68%) and heptane (e.g., reduction improvement of 12% to 28%) compared to the 100% heptane solvent. However, microparticles produced with the 50% heptane/50% ethanol solvent combination had poor handling characteristics, while the 90% heptane/10% ethanol solvent combination resulted in microparticles with acceptable handling characteristics.

TABLE 8

| Hardening Solvent | Batch Reference | RESIDUAL SOLVENT LEVELS | | |
| --- | --- | --- | --- | --- |
| | | Methylene Chloride Wt % | Ethanol Wt % | Heptane Wt % |
| Heptane 100% | 1A | 5.21 | N/A | 0.94 |
| | 2A | 3.2 | N/A | 1.2 |
| Heptane 90% + Ethanol 10% | 1B | 2.79 | 1.34 | 0.82 |
| | 2B | 1.04 | 0.58 | 1.06 |
| Heptane 50% + Ethanol 50% | 1C | 2.72 | 1.48 | 0.68 |

Example 9

Two batches of microparticles (Batches 1 and 2) were prepared using a two-step quench (or harden)/wash process, consisting of a heptane quench step followed by an ethanol wash step. Batch 1 was prepared at a 100 gram scale, containing 1% sucrose. Batch 2 was prepared at a 10 gram scale in the same manner as described below for Batch 1.

The microparticles were manufactured by a phase separation process. The polymer solution was prepared by dissolving 98 g 50:50 poly(d,l-lactic-co-glycolic acid), MEDISORB® 5050DL 4A polymer, molecular weight of approximately 50 kD (Alkermes, Inc.) in 1533 g methylene chloride. The sucrose encapsulate solution was prepared by dissolving 0.98 grams sucrose in 21 grams deionized water. The polymer and sucrose solutions were mixed and probe sonicated for 3 minutes to form a water-in-oil emulsion. The emulsion was added to a 3-liter stainless steel reactor. The stir speed was set to 2100 RPM. The polymeric precipitant (coacervating agent), 350 centistoke silicone oil (Dow Corning), was added to the reactor to induce phase separation. Addition was discontinued after adding a total of 1534 g over a time period of approximately 4.25 minutes. The embryonic microparticles were gravity transferred into a 35-liter heptane quench at 20° C. After about 1 hour in the heptane quench, the agitation was terminated to allow the microparticles to sediment. The heptane was decanted via a peristaltic pump. The microparticle washing stage was initiated by charging the concentrated slurry with 14.7 kg ethanol. After 2 hours, the microparticles were collected and dried for three days using a nitrogen purge.

Two batches of microparticles were prepared by a one-step quench (or harden) and wash process in accordance with the method described above and shown in FIG. 3. For Batch 3, the polymer solution was prepared by dissolving 98 g 50:50 poly(d,l-lactic-co-glycolic acid), MEDISORB® 5050DL 4A polymer, molecular weight of approximately 50 kD (Alkermes, Inc.) in 1536 g methylene chloride. The sucrose encapsulate solution was prepared by dissolving 1.0 gram sucrose in 20 grams deionized water. The polymer and sucrose solutions were mixed and probe sonicated for 2 minutes to form a water-in-oil emulsion. The emulsion was added to a 3-liter stainless steel reactor. The stir speed was set to 1730 RPM. The polymeric precipitant (coacervating agent), 1000 centistoke silicone oil (Dow Corning), was added to the reactor to induce phase separation. Addition was discontinued after adding a total of 1534 g over a time period of approximately 5 minutes. The embryonic microparticles were gravity transferred into a 24 kg quench made up of 90% heptane and 10% ethanol at 5° C. After about 1 hour in the heptane quench, the agitation was terminated to allow the microparticles to sediment. The heptane/ethanol was decanted via a peristaltic pump. The microparticles were rinsed with 12.6 kg heptane for 1 hour, collected, and dried for three days using a nitrogen purge.

For Batch 4, 101.3 mg of sucrose and 99 mg AC2993 were dissolved in 2 g acetate buffer (pH 4). 9.8 g of polymer, poly(d,l-lactic-co-glycolic acid), MEDISORB® 5050DL 4A polymer, molecular weight of approximately 50 kD (Alkermes, Inc.) was weighed and dissolved in 153 g of methylene chloride in an Erlenmeyer flask. The aqueous phase was added to the organic phase using syringe/needle and sonicated for 1 minute. Sonication was repeated twice with a 3 minute gap in between. The resulting emulsion was transferred into a coacervation reactor, and stirred at 1617 RPM using an impeller. 225 g of dimethicone (1000 centistoke) was transferred to the reactor using a peristaltic pump over a period of 25 minutes. The contents were mixed for 15 minutes at 1617 RPM. The coacervate dispersion was transferred by gravity into another tank containing 3600 g of heptane and 400 g ethanol stirred at approximately 800 RPM, and at a temperature of 3.9° C. After 90 minutes, stirring was stopped, and the microparticles were allowed to settle. The supernant was decanted. 2000 g of fresh pre-chilled heptane (5° C.) was added to the tank, and the agitation was continued for 1 hour. The tank was pressurized, and the product was collected in a cone filter assembly at 3° C. A final rinse/filtration was performed with 1000 g of fresh pre-chilled heptane. Drying was performed at 3°, 25°, and 35° C. in a static cone dryer.

The residual solvent levels for Batches 1-4 are shown below in Table 9. Table 9 shows the residual solvent data for microparticles prepared using separate hardening and wash steps, and a 90% heptane/10% ethanol solvent combination step. As shown in Table 9, the 90% heptane/10% ethanol solvent combination step produced microparticles with lower levels of methylene chloride (e.g., reduction improvement of 55% to 56%) and heptane (e.g., reduction improvement of 16% to 58%) compared with the separate hardening and wash steps.

TABLE 9

RESIDUAL SOLVENT LEVELS

| Process | Batch Reference | Methylene Chloride Wt % | Ethanol Wt % | Heptane Wt % |
|---|---|---|---|---|
| 2 step quench/wash process | 1 | 0.9 | 0.2 | 3.1 |
| | 2 | 2.2 | 0.2 | 2.5 |
| 1 step quench/wash process | 3 | 0.4 | 0.1 | 2.6 |
| | 4 | 1.0 | 0.67 | 1.04 |

Preferred active agents that can be encapsulated by the process of the present invention include peptides. Preferred peptides include luteinizing-hormone-releasing-hormone analogues, such as goserelin, and exendin and exendin analogues. Other preferred active agents include 1,2-benzazoles, more particularly, 3-piperidinyl-substituted 1,2-benzisoxazoles and 1,2-benzisothiazoles, including 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one ("risperidone") and 3-[2-[4-(6-fluoro-1,2-benzisoxazol-3-yl)-1-piperidinyl]ethyl]-6,7,8,9-tetrahydro-9-hydroxy-2-methyl-4H-pyrido[1,2-a]pyrimidin-4-one ("9-hydroxyrisperidone") and the pharmaceutically acceptable salts thereof. Risperidone (which term, as used herein, is intended to include its pharmaceutically acceptable salts) is most preferred. Risperidone can be prepared in accordance with the teachings of U.S. Pat. No. 4,804,663, the entirety of which is incorporated herein by reference. 9-hydroxyrisperidone can be prepared in accordance with the teachings of U.S. Pat. No. 5,158,952, the entirety of which is incorporated herein by reference.

Preferred examples of polymer matrix materials include poly(glycolic acid), poly(d,l-lactic acid), poly(l-lactic acid), copolymers of the foregoing, and the like. Various commercially available poly(lactide-co-glycolide) materials (PLGA) may be used in the method of the present invention. For example, poly (d,l-lactic-co-glycolic acid) is commercially available from Alkermes, Inc. (Blue Ash, Ohio). A suitable product commercially available from Alkermes, Inc. is a 50:50 poly(d,l-lactic-co-glycolic acid) known as MEDISORB® 5050 DL. This product has a mole percent composition of 50% lactide and 50% glycolide. Other suitable commercially available products are MEDISORB® 6535 DL, 7525 DL, 8515 DL, 9010DL and poly(d,l-lactic acid) (100 DL). Poly(lactide-co-glycolides) are also commercially available from Boehringer Ingelheim (Germany) under its Resomerg mark, e.g., PLGA 50:50 (Resomer® RG 502), PLGA 75:25 (Resomer® RG 752) and d,l-PLA (Resomerg RG 206), and from Birmingham Polymers (Birmingham, Ala.). These copolymers are available in a wide range of molecular weights and ratios of lactic acid to glycolic acid.

The molecular weight of the polymeric matrix material is of some importance. The molecular weight should be high enough to permit the formation of satisfactory polymer coatings, i.e., the polymer should be a good film former. Usually, a satisfactory molecular weight is in the range of 5,000 to 500,000 daltons, preferably from about 50,000 to 150,000 daltons. However, since the properties of the film are also partially dependent on the particular polymeric matrix material being used, it is very difficult to specify an appropriate molecular weight range for all polymers. The molecular weight of the polymer is also important from the point of view of its influence upon the biodegradation rate of the polymer and the desired drug release duration of the product.

The formulation prepared by the process of the present invention contains an active agent dispersed in the microparticle polymeric matrix material. The amount of such agent incorporated in the microparticles usually ranges from about 1 wt. % to about 90 wt. %.

Other biologically active agents suitable for use with the present invention include non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-Parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodienone, meperidine, morphine and the like; non-narcotics such as salicylates, aspirin, acetaminophen, d-propoxyphene and the like; opioid receptor antagonists, such as naltrexone and naloxone; antibiotics such as gentamycin, tetracycline and penicillins; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs.

Still other suitable active agents include estrogens, antibacterials; antifungals; antivirals; anticoagulants; anticonvulsants; antidepressants; antihistamines; and immunological agents.

Other examples of suitable biologically active agents include peptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, enzymes (e.g., superoxide dismutase, tissue plasminogen activator), tumor suppressors, blood proteins, hormones and hormone analogs (e.g., growth hormone, adrenocorticotropic hormone and luteinizing hormone releasing hormone (LHRH)), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules; oligonucleotides; and ribozymes. Small molecular weight agents suitable for use in the invention include, antitumor agents such as bleomycin hydrochloride, carboplatin, methotrexate and adriamycin; antipyretic and analgesic agents; antitussives and expectorants such as ephedrine hydrochloride, methylephedrine hydrochloride, noscapine hydrochloride and codeine phosphate; sedatives such as chlorpromazine hydrochloride, prochlorperazine hydrochloride and atropine sulfate; muscle relaxants such as tubocurarine chloride; antiepileptics such as sodium phenyloin and ethosuximide; antiulcer agents such as metoclopramide; antidepressants such as clomipramine; antiallergic agents such as diphenhydramine; cardiotonics such as theophillol; antiarrhythmic agents such as propranolol hydrochloride; vasodilators such as diltiazem hydrochloride and bamethan sulfate; hypotensive diuretics such as pentolinium and ecarazine hydrochloride; antidiuretic agents such as metformin; anticoagulants such as sodium citrate and heparin; hemostatic agents such as thrombin, menadione sodium bisulfite and acetomenaphthone; antituberculous agents such as isoniazide and ethanbutol; hormones such as prednisolone sodium phosphate and methimazole.

Conclusion

While various embodiments of the present invention have been described above, it should be understood that they have been presented by way of example only, and not limitation. The present invention is not limited to a particular active agent, polymer or solvent, nor is the present invention limited to a particular scale or batch size. Thus, the breadth and scope of the present invention should not be limited by any of the above-described exemplary embodiments, but should be defined only in accordance with the following claims and their equivalents.

What is claimed is:

1. A method for preparing microparticles, comprising:
combining a peptide solution and a polymer solution to form an emulsion, wherein the peptide solution comprises sucrose and exendin or an exendin analog, and the polymer solution comprises a biodegradable, biocompatible polymer dissolved in a halogenated solvent;
combining the emulsion with a coacervating agent that is free from solvents for the polymer to form a combined phase;
extracting the halogenated solvent from the combined phase with an extraction medium of a 9:1 ratio of heptane to ethanol, whereby microparticles precipitate out of the extraction medium; and
rinsing the microparticles with a blend of ethanol and heptane to thereby reduce the level of residual halogenated solvent.

2. The method of claim 1, wherein the coacervating agent is silicone oil.

3. The method of claim 1, wherein the coacervating agent is dimethicone.

4. The method of claim 1, wherein the polymer is selected from the group consisting of poly(glycolic acid), poly(d,l-lactic acid), poly(l-lactic acid), and copolymers of the foregoing.

5. The method of claim 4, wherein the polymer is poly(d,l-lactic-co-glycolic acid).

6. The method of claim 1, wherein the rinsing step is carried out until the level of residual halogenated solvent in the microparticles is less than about 0.06% by weight.

7. The method of claim 1, further comprising after said rinsing step:
final drying of the microparticles.

8. The method of claim 1, wherein the step of combining the peptide solution and the polymer solution is carried out using a static mixer.

9. A method for preparing microparticles, comprising:
combining a peptide solution and a polymer solution to form an emulsion, wherein the peptide solution comprises sucrose and exendin or an exendin analog, and the polymer solution comprises a 50:50 poly(d,l-lactic-co-glycolic acid) polymer dissolved in methylene chloride;
combining the emulsion with silicone oil to form a combined phase;
extracting the methylene chloride from the combined phase with an extraction medium of a 9:1 ratio of heptane to ethanol, whereby microparticles precipitate out of the extraction medium; and
rinsing the microparticles with a blend of ethanol and heptane to thereby reduce the level of methylene chloride.

10. The method of claim 9, wherein the rinsing step is carried out until the level of residual methylene chloride in the microparticles is less than about 0.06% by weight.

11. The method of claim 9, further comprising after said rinsing step:
final drying of the microparticles.

12. The method of claim 9, wherein the step of combining the peptide solution and the polymer solution is carried out using a static mixer.

* * * * *